United States Patent [19]

Glamkowski et al.

[11] Patent Number: 4,929,615

[45] Date of Patent: May 29, 1990

[54] 7H-BENZO[B]PYRAZINO[1,2-D]PYR-ROLO[3,2,1-JK][1,4]BENZODIAZEPINES

[75] Inventors: Edward J. Glamkowski, Warren; Barbara E. Kurys, Elmwood Park, both of N.J.

[73] Assignee: Hoechst-Roussel Pharmaceuticals Inc., Somerville, N.J.

[21] Appl. No.: 364,395

[22] Filed: Jun. 12, 1989

[51] Int. Cl.$^5$ .................... C07D 487/06; A61K 31/55
[52] U.S. Cl. .................................. 514/219; 540/556; 540/555
[58] Field of Search .................... 540/556; 514/219

[56] References Cited

U.S. PATENT DOCUMENTS

| 4,186,199 | 1/1980 | Glamkowski | 424/232 |
| 4,192,874 | 3/1980 | Glamkowski | 424/248.54 |
| 4,472,414 | 9/1984 | Glamkowski | 424/267 |
| 4,663,453 | 5/1987 | Glamkowski | 540/556 |
| 4,751,223 | 6/1988 | Glamkowski | 514/219 |
| 4,761,411 | 8/1988 | Glamkowski | 514/219 |
| 4,840,947 | 6/1989 | Glamkowski | 514/214 |

Primary Examiner—Mukund J. Shah
Assistant Examiner—Philip Datlow
Attorney, Agent, or Firm—Raymond R. Wittekind

[57] ABSTRACT

Novel 7H-benzo[b]pyrazino[1,2-d]pyrrolo[3,2,1-jk][1,4]benzodiazepines, processes for the preparation thereof, and a method of treating depression utilizing compounds or compositions thereof are disclosed.

8 Claims, No Drawings

7H-BENZO[B]PYRAZINO[1,2-D]PYRROLO[3,2,1-JK][1,4]BENZODIAZEPINES

The present invention to 7H-benzo[b]pyrazino[1,2-d]pyrrolo[3,2,1-jk]-[1,4]benzodiazepines. More particularly, the present invention relates to 7H-benzo[b-]pyrazino[1,2-d]pyrrolo[3,2,1-jk][1,4]benzodiazepines of the formula

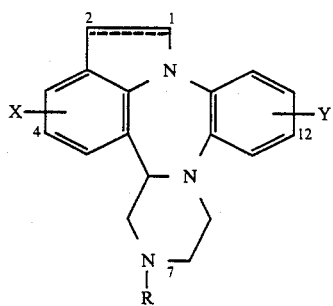

wherein R is hydrogen, loweralkyl, or a group of the formula $COO(CR^1Z)_mCR^2R^3R^4$ wherein $R^1$, $R^2$, $R^3$ and $R^4$ are independently hydrogen or loweralkyl, Z is hydrogen, loweralkyl, or halogen, and m is 0 or 1; X and Y are independently hydrogen, halogen, loweralkyl or trifluoromethyl; the dotted line represents an optional carbon-to-carbon bond; an optical isomer thereof, or a pharmaceutically acceptable acid addition salt thereof, which are useful for treating depression alone or in combination with inert adjuvants.

Subgeneric to the 7H-benzo[b]pyrazino[1,2-d]pyrrolo[3,2,1-jk]-[1,4]benzodiazepines of the present invention are compounds wherein:
(a) R is hydrogen or loweralkyl; and
(b) R is a group of the formula $COO(CR^1Z)_mCR^2R^3R^4$ wherein $R^1$, $R^2$, $R^3$ and $R^4$ are independently hydrogen or loweralkyl, Z is hydrogen, loweralkyl, or halogen, and m is 0 or 1.

The present invention also relates to 1,2-dihydrobenzo[b]pyrazino[1,2-d]pyrrolo[3,2,1-jk][1,4]benzodazepin-8,9(6H)-diones of the formula

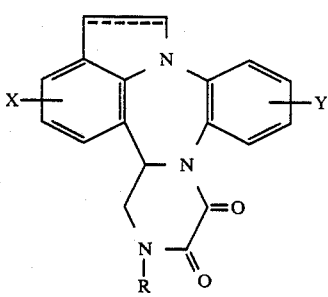

wherein R is hydrogen or loweralkyl; and X and Y are independently hydrogen, halogen, loweralkyl or trifluoromethyl; the dotted line represents an optional carbon-to-carbon bond; or an optical isomer thereof, which are useful as intermediates for the synthesis of the present 7-benzo[b]pyrazino[1,2-d]pyrrolo[3,2,1-jk][1,4]benzodiazepines.

As used through the specification and appended claims, the term "alkyl" refers to a straight or branched chain hydrocarbon radical containing no unsaturation and having 1 to 8 carbon atoms such as methyl, ethyl, 1-propyl, 1-butyl, 1-pentyl, 2-pentyl, 3-hexyl, 4-heptyl, 2-octyl, and the like; the term "alkanol" refers to a compound formed by a combination of an alkyl group and a hydroxyl radical. Examples of alkanols are methanol, ethanol, 1- and 2-propanol, 2,2-dimethylethanol, hexanol, octanol, and the like. The term "halogen" refers to a member of the family consisting of fluorine, chlorine, bromine or iodine. The term "lower" as applied to any of the aforementioned groups refers to a group having a carbon skeleton of 1 to 6 carbon atoms.

The compounds of the present invention which lack an element of symmetry exist as optical antipodes and as the racemic forms thereof. Optical antipodes may be prepared from the corresponding racemic forms by standard optical resolution techniques, involving, for example, the separation of diastereomeric salts of those instant compounds characterized by the presence of a basic amino group and an optically active acid, or by the synthesis from optically active precursors.

The present invention comprehends all optical isomers and racemic forms thereof of the compounds disclosed and claimed herein. The formulas of the compounds shown herein are intended to encompass all possible optical isomers of the compounds so depicted.

The novel 7H-benzo[b]pyrazino[1,2-d]pyrrolo[3,2,1-jk][1,4]benzodiazepines of the present invention are prepared by processes illustrated in the Reaction Scheme.

To synthesize the parent hexahydro-7H-benzo[b-]pyrazino[1,2-d]pyrrolo[3,2,1-jk][1,4]benzodiazepine system, i.e., a benzodiazepine 5 wherein X and Y are as hereinbeforedescribed, a 6-aminomethyl-1,2,6,7-tetrahydrobenzo[b]pyrrolo[3,2,1-jk][1,4]benzodiazepine 1, the preparation of which is described in U.S. Pat. No. 4,751,223 issued June 14, 1988, is condensed with a dialkyl oxalate 7

wherein $R^5$ is alkyl to provide a pyrazinobenzodiazepin-8,9(6H)-dione 2 wherein R is loweralkyl which is reduced to a pyrazinobenzodiazepine 3 wherein R is loweralkyl. Pyrazinobenzodiazepine 3 wherein R is as hereinbeforedescribed may be dealkylated to the parent system 5 via carbamate 4.

The condensation is performed by contacting a benzodiazepine 1 with a dialkyl oxalate 7 at a reaction temperature of about 100° C. to about 200° C., a reaction temperature of about 140° C. to about 180° C. being preferred.

The reduction is accomplished by contacting a pyrazinobenzodiazepin-8,9(6H)-dione 2 with diborane in a suitable solvent. Among suitable solvents, there may be mentioned ethereal solvents such as dioxane, tetrahydrofuran, 1,2-dimethoxyethane, diethyleneglycol dimethylether, and the like. Tetrahydrofuran is the preferred solvent. While the reduction temperature is not narrowly critical, the reduction is conveniently performed at the reflux temperature of the reaction medium.

The dealkylation may be carried out by conventional methods, for example, by reacting a pyrazinobenzodiazepine 3 with a haloformate 8.

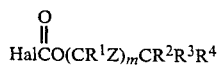

wherein $R^1$, $R^2$, $R^3$, $R^4$, Z, and m are as hereinbeforedescribed and Hal is chloro or bromo to provide a carbamate 4, which may be cleaved to the parent pyrazinobenzodiazeine 5 by acid or base hydrolysis when Z is hydrogen or loweralkyl, or an alkanol when Z is halogen. For the latter process, see R. A. Olofson, et al., J. Org. Chem., 49, 2081 (1984).

To elaborate the tetrahydro-7H-benzo[b]pyrazino[1,2-d]pyrrolo[3,2,1-jk][1,4]benzodiazepine system, i.e., a benzodiazepine 6 wherein R, X, and Y are as hereinbeforedescribed, a hexahydro-7H-benzo[b]pyrazino[1,2-d]pyrrolo[3,2,1-jk][1,4]benzodiazepine 3 or 5, may be dehydrogenated by a benzoquinone, for example, a 2,3-dichloro-5,6-dicyano-1,4-benzoquinone by methods known in the art. See, for example, E. J. Glamkowski, et al., J. Heterocyclic Chem., 16, 865 (1979).

The utility of the compounds of the present invention in the treatment of depression in mammals is demonstrated by their ability to inhibit tetrabenazine induced ptosis in mice [International Journal of Neuropharmacology, 8, 73 (1969)], a standard assay for antidepressant activity. Thus, for instance an intraperitoneal dose of 14.9 mg/kg of body weight of 1,2,5b,6,8,9-hexahydro-7-methyl-7H-benzo[b]pyrazino[1,2-d]pyrrolo[3,2,1-jk][1,4]benzodiazepine dihydrochloride elicits a 50% inhibition of tetrabenazine induced ptosis in mice. A standard antidepressant, imipramine, elicits a 50% inhibition of ptosis in mice at an intraperitoneal dose of 1.28 mg/kg of body weight.

Antidepressant production is achieved when the present 7H-benzo[b]pyrazino[1,2-d]pyrrolo[3,2,1-jk][1,4]benzodiazepines are administered to a subject requiring such treatment as an effective oral, parenteral or intravenous dose of from 0.01 to 100 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Compounds of the invention also include:

(a) 1,2,5b,6,8,9-hexahydro-7H-benzo[b]pyrazino[1,2-d]pyrrolo[3,2,1-jk][1,4]benzodiazepine;
(b) 12-fluoro-1,2,5b,6,8,9-hexahydro-7-methyl-7H-benzo[b]pyrazino[1,2-d]pyrrolo[3,2,1-jk][1,4]benzodiazepine;
(c) 12-chloro-1,2,5b,6,8,9-hexahydro-7-methyl-7H-benzo[b]pyrazino[1,2-d]pyrrolo[3,2,1-jk][1,4]benzodiazepine;
(d) 12-bromo-1,2,5b,6,8,9-hexahydro-7-methyl-7H-benzo[b]pyrazino[1,2-d]pyrrolo[3,2,1-jk][1,4]benzodiazepine;
(e) 1,2,5b,6,8,9-hexahydro-7,12-dimethyl-7H-benzo[b]pyrazino[1,2-d]pyrrolo[3,2,1-jk][1,4]benzodiazepine;
(f) 1,2,5b,6,8,9-hexahydro-7-methyl-12-trifluoromethyl-7H-benzo[b]pyrazino[1,2-d]pyrrolo[3,2,1-jk][1,4]benzodiazepine;
(g) 4,12-dibromo-1,2,5b,6,8,9-hexahydro-7-methyl-7H-benzo[b]pyrazino[1,2-d]pyrrolo[3,2,1-jk][1,4]benzodiazepine;
(h) 4,12-dibromo-5b,6,8,9-tetrahydro-7-methyl-7H-benzo[b]pyrazino[1,2-d]pyrrolo[3,2,1-jk][1,4]benzodiazepine;
(i) 5b,6,8,9-tetrahydro-4,7-dimethyl-7H-benzo[b]pyrazino[1,2-d]pyrrolo[3,2,1-jk][1,4]benzodiazepine;
(j) 5b,6,8,9-tetrahydro-7-methyl-7H-benzo[b]pyrazino[1,2-d]pyrrolo[3,2,1-jk][1,4]benzodiazepine;
(k) 1,2,5b,6,8,9-hexahydro-4-trifluoromethyl-7H-benzo[b]pyrazino[1,2-d]pyrrolo[3,2,1-jk][1,4]benzodiazepine;
(l) 7-ethoxycarbonyl-1,2,5b,6,8,9-hexahydro-7H-benzo[b]pyrazino[1,2-d]pyrrolo[3,2,1-jk][1,4]benzodiazepine;
(m) 1,2,5b,6,8,9-hexahydro-7-methoxycarbonyl-7H-benzo[b]pyrazino[1,2-d]pyrrolo[3,2,1-jk][1,4]benzodiazepine;
(n) 1,2,5b,6,8,9-hexahydro-7-(1-chloroethoxycarbonyl)-7H-benzo[b]pyrazino[1,2-d]pyrrolo[3,2,1-jk][1,4]benzodiazepine;
(o) 1,2-dihydrobenzo[b]pyrazino[1,2-d]pyrrolo[3,2,1-jk][1,4]benzodiazepine-8,9(6H)-dione;
(p) 4,12-dibromo-1,2-dihydrobenzo[b]pyrazino[1,2-d]pyrrolo[3,2,1-jk][1,4]benzodiazepine-8,9(6H)-dione;
(q) 1,2-dihydro-4,7,12-trimethylbenzo[b]pyrazino[1,2-d]pyrrolo[3,2,1-jk][1,4]benzodiazepine-8,9(6H)-dione;
(r) 1,2-dihydro-4-trifluoromethylbenzo[b]pyrazino][1,2-d]pyrrolo[3,2,1-jk][1,4]benzodiazepine-8,9(6H)-dione; and
(s) 1,2-dihydro-12-trifluoromethylbenzo[b]pyrazino[1,2-d]pyrrolo[3,2,1-jk][1,4]benzodiazepine-8,9(6H)-dione.

Effective amounts of the compounds of the present invention may be administered to a subject by any one of the several methods, for example, orally as in capsules or tablets, parenterally in the form of sterile solutions or suspensions, and in some cases intravenously in the form of sterile solutions. The 7H-benzo[b]pyrazino[1,2-d]pyrrolo[3,2,1-jk][1,4]benzodiazepines of the present invention, while effective themselves, may be formulated and administered in the form of their pharmaceutically acceptable addition salts for purposes of stability, convenience of crystallization, increased solubility, and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysucinic acid, citric acid and the like.

Effective quantities of the compounds of the invention may be administered orally, for example, with an inert diluent or with an edible carrier. They may be enclosed in gelatin capsules or compressed into tablets. For the purposes of oral therapeutic administration, the aforesaid compounds may be incorporated with an excipient and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0–300 milligrams of the active compound.

The tablets, pills, capsules, troches and the like may also contain the following ingredients: a binder such as microcrystalline cellulose, gum tragacanth or gelatine, an excipient such as starch or lactose, a disintegrating agent such as alginic acid, corn starch and the like, a lubricant such as magnesium stearate, a glidant such as colloidal silicon dioxide; and a sweetening agent such as sucrose or saccharin, or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example as coatings. Thus tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes only and are not to be construed as limiting the invention.

EXAMPLE 1

1,2-Dihydro-7-methylbenzo[b]pyrazino[1,2-d]pyrrolo[3,2,1-jk][1,4]benzodiazepin-8,9(6H)-dione N-methyl-1,2,6,7-tetrahydrobenzo[b]pyrrolo[3,2,1-jk][1,4]benzodiazepine-6-methanamine (2.5 g), and diethyl oxalate (1.6 g), were combined and heated to 140° C. over a period of 45 min, then to 180° C. over 15 min. The reaction mixture was maintained at this temperature for 1 hr. The reaction mixture was cooled, dissolved in a small volume of dichloromethane, placed on a column of silica gel and eluted with 2.5% methanol-dichloromethane to yield 1.4 g, (46.7%) of product.

Recrystallization from methanol gave the analytical sample, m.p. >80° C.

ANALYSIS: Calculated for $C_{19}H_{17}N_3O_2$: 71.45%C, 5.38%H, 13.16% N. Found: 71.32%C, 5.36%H, 12.92%N.

EXAMPLE 2

1,2,5b,6,8,9-Hexahydro-7-methyl-7H-benzo[b]pyrazino[1,2-d]pyrrolo[3,2,1-jk][1,4]benzodiazepine 1,2-Dihydro-7-methylbenzo[b]pyrazino[1,2-d]pyrrolo[3,2,1-jk][1,4]benzodiazepine-8,9(6H)-dione (10 g), was added to a solution of diborane (200 ml, 1M in tetrahydrofuran), under nitrogen, and the mixture was refluxed for 1 hr. Ethanol (96%, 50 ml) was slowly added, and the solution was evaporated. The residue was dissolved in 18% hydrochloric acid (180 ml). The solution was heated on a steam bath for 1 hr, cooled, made basic with 30% sodium hydroxide solution, and extracted with dichloromethane. The extract was washed with water, dried over anhydrous sodium sulfate and evaporated to give 7.7 g, (84.9%) of product as the free base.

The free base was converted to the dihydrochloride with methanolic-hydrogen chloride-ether. Recrystallization from ethanol gave the analytical sample, mp 251°–252° (dec).

ANALYSIS: Calculated for $C_{19}H_{21}N_3 \cdot 2HCl$: 62.63%C, 6.38%H, 11.53%N. Found: 62.83%C, 6.53%H, 11.70%N.

REACTION SCHEME

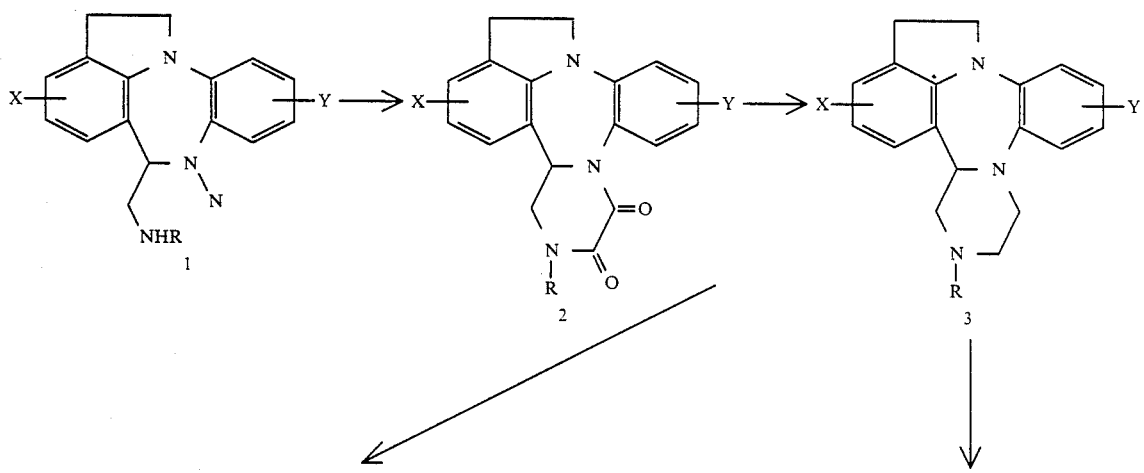

-continued
REACTION SCHEME

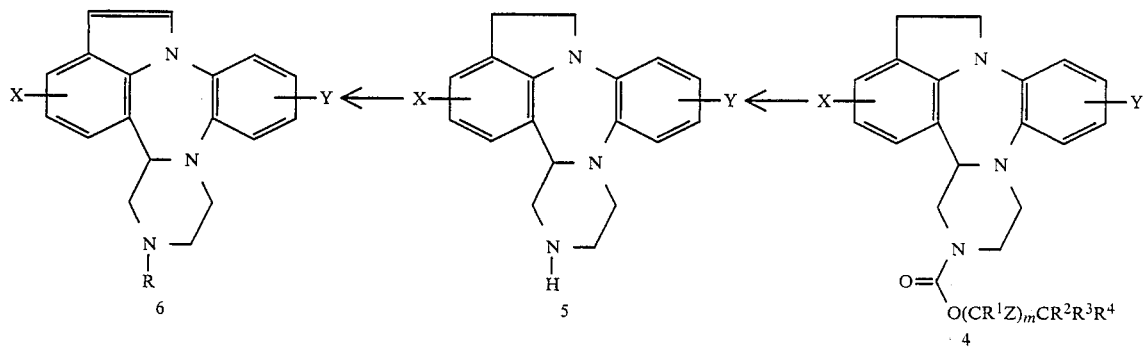

wherein R, $R^1$, $R^2$, $R^3$, $R^4$, X, Y, Z, and m are as hereinbeforementioned.

We claim:

1. A compound of the formula

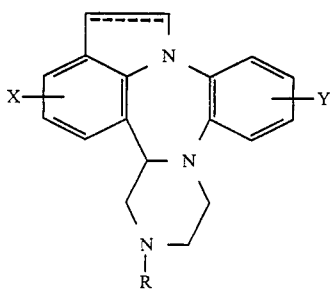

wherein R is hydrogen, loweralkyl, or a group of the formula $COO(CR^1Z)_m CR^2R^3R^4$ wherein $R^1$, $R^2$, $R^3$ and $R^4$ are hydrogen or loweralkyl, Z is hydrogen, loweralkyl, or halogen, and m is 0 or 1; X and Y are independently hydrogen, halogen, loweralkyl, or trifluoromethyl; the dotted line represents an optional carbon-to-carbon bond; an optical isomer thereof, or a pharmaceutically acceptable acid addition salt thereof.

2. A compound according to claim 1 wherein R is hydrogen or loweralkyl.

3. A compound according to claim 1 wherein R is a group of the formula $COO(CR^1Z)_m CR^2R^3R^4$ wherein $R^1$, $R^2$, $R^3$ and $R^4$ are independently hydrogen or loweralkyl, Z is hydrogen, loweralkyl, or halogen, and m is 0 or 1.

4. The compound according to claim 2 which is 1,2,5b,6,8,9-hexahydro-7-methyl-7H-benzo[b-]pyrazino[1,2-d]pyrrolo[3,2,1-jk][1,4]benzodiazepine.

5. A compound of the formula

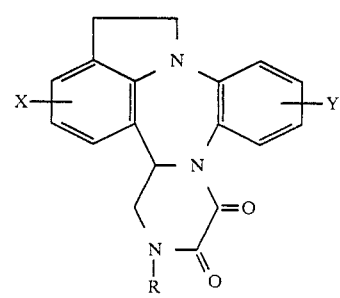

wherein R is hydrogen or loweralkyl; and X and Y are independently hydrogen, halogen, loweralkyl, or trifluoromethyl, or a optical isomer thereof.

6. The compound according to claim 5 which is 1,2-dihydro-7-methylbenzo[b]pyrazino[1,2-d]pyrrolo[3,2,1-jk][1,4]benzodiazepin-8,9(6H)-dione.

7. A method of treating depression comprising administering to a mammal in need of depression treatment a depression treating effective amount of a compound according to claim 1.

8. A depression treating composition comprising an inert depression treating adjuvant and, as the active ingredient, an amount effective in treating depression of a compound according to claim 1.

* * * * *